ical Application No. PCT/JP2016/
(12) United States Patent
Ushijima

(10) Patent No.: US 10,574,971 B2
(45) Date of Patent: Feb. 25, 2020

(54) IMAGE CALIBRATION INSPECTION TOOL AND ENDOSCOPE SYSTEM

(71) Applicant: OLYMPUS CORPORATION, Tokyo (JP)

(72) Inventor: Takanori Ushijima, Tama (JP)

(73) Assignee: OLYMPUS CORPORATION, Tokyo (JP)

(*) Notice: Subject to any disclaimer, the term of this patent is extended or adjusted under 35 U.S.C. 154(b) by 177 days.

(21) Appl. No.: 15/703,343

(22) Filed: Sep. 13, 2017

(65) Prior Publication Data

US 2018/0007346 A1 Jan. 4, 2018

Related U.S. Application Data

(63) Continuation of application No. PCT/JP2016/060061, filed on Mar. 29, 2016.

(30) Foreign Application Priority Data

Sep. 25, 2015 (JP) ................................. 2015-188658

(51) Int. Cl.
*H04N 13/246* (2018.01)
*G02B 23/24* (2006.01)
(Continued)

(52) U.S. Cl.
CPC ............ *H04N 13/246* (2018.05); *A61B 1/005* (2013.01); *A61B 1/00009* (2013.01); *A61B 1/00039* (2013.01); *A61B 1/00045* (2013.01); *A61B 1/00057* (2013.01); *A61B 1/00112* (2013.01); *A61B 1/05* (2013.01); *B23K 26/0006* (2013.01); *B23K 26/355* (2018.08);
(Continued)

(58) Field of Classification Search
None
See application file for complete search history.

(56) References Cited

U.S. PATENT DOCUMENTS 8,382,300 B2   2/2013   Mase
8,913,114 B2  12/2014   Yoshino
(Continued)

FOREIGN PATENT DOCUMENTS

CA    2 331 240 A1    7/2001
CN    102338897 A     2/2012
(Continued)

OTHER PUBLICATIONS

International Search Report dated Jun. 15, 2016 received in International Application No. PCT/JP2016/060061, together with an English-language translation.
(Continued)

*Primary Examiner* — Pankaj Kumar
*Assistant Examiner* — Charles N Hicks
(74) *Attorney, Agent, or Firm* — Scully, Scott, Murphy & Presser, P.C.

(57) ABSTRACT

An image calibration inspection tool includes: a plurality of substantially rectangular markers, two orthogonal sides of which are connected by an arc-shaped curve; and a calibration chart in which the plurality of markers are formed on a metal plate through machining, laser marking, or the like, wherein two of the markers in a diagonal direction are separated by a predetermined distance.

10 Claims, 10 Drawing Sheets

(51) Int. Cl.
*A61B 1/00* (2006.01)
*B23K 26/352* (2014.01)
*B23K 26/00* (2014.01)
*B23K 26/361* (2014.01)
*H04N 13/296* (2018.01)
*A61B 1/005* (2006.01)
*A61B 1/05* (2006.01)
*H04N 5/225* (2006.01)
*A61B 17/00* (2006.01)
*B23K 101/20* (2006.01)

(52) U.S. Cl.
CPC ............ B23K 26/361 (2015.10); G02B 23/24 (2013.01); H04N 5/2256 (2013.01); H04N 13/296 (2018.05); *A61B 2017/00725* (2013.01); *B23K 2101/20* (2018.08); *H04N 2005/2255* (2013.01)

(56) References Cited

U.S. PATENT DOCUMENTS

| | | | |
|---|---|---|---|
| 2005/0017162 A1 | 1/2005 | Nagakubo et al. | |
| 2007/0240325 A1 | 10/2007 | Pelsue et al. | |
| 2008/0004492 A1 | 1/2008 | Nakamura et al. | |
| 2008/0097156 A1* | 4/2008 | Nakamura | A61B 1/045 600/117 |
| 2010/0048993 A1* | 2/2010 | Shidara | A61B 1/00057 600/109 |
| 2012/0007985 A1* | 1/2012 | Inui | H04N 17/002 348/148 |
| 2013/0256284 A1 | 10/2013 | Ellin et al. | |
| 2014/0022365 A1 | 1/2014 | Yoshino | |
| 2016/0048953 A1* | 2/2016 | Zhao | G01D 1/00 382/103 |
| 2016/0094840 A1* | 3/2016 | Warner | H04N 17/002 348/188 |
| 2017/0070725 A1* | 3/2017 | Kishiwada | H04N 13/246 |

FOREIGN PATENT DOCUMENTS

| | | |
|---|---|---|
| CN | 103841877 A | 6/2014 |
| EP | 1 839 554 A1 | 10/2007 |
| EP | 2 752 150 A1 | 7/2014 |
| JP | 10-322562 A | 12/1998 |
| JP | 2001-056586 A | 2/2001 |
| JP | H10-315521 A | 11/2001 |
| JP | 2004-177149 A | 6/2004 |
| JP | 2007-306945 A | 11/2007 |
| JP | 2008-104877 A | 5/2008 |
| JP | 2009-268657 A | 11/2009 |
| JP | 2015-6282 A | 1/2015 |
| WO | 2006/077965 A1 | 7/2006 |
| WO | 2013/175861 A1 | 11/2013 |

OTHER PUBLICATIONS

Extended Supplementary European Search Report dated Sep. 21, 2018 in European Patent Application No. 16 84 8348.5.

* cited by examiner

IMAGE CALIBRATION INSPECTION TOOL AND ENDOSCOPE SYSTEM

CROSS REFERENCE TO RELATED APPLICATION

This application is a continuation application of PCT/JP2016/060061 filed on Mar. 29, 2016 and claims benefit of Japanese Application No. 2015-188658 filed in Japan on Sep. 25, 2015, the entire contents of which are incorporated herein by this reference.

BACKGROUND OF THE INVENTION

1. Field of the Invention

The present invention relates to an image calibration inspection tool and an endoscope system configured to correct an observation system.

2. Description of the Related Art

Conventionally, endoscopes including insertion portions that can be inserted into subjects are used, the endoscopes allowing observers to observe the subjects that cannot be directly visually checked. Among the endoscopes, there is a binocular 3D endoscope capable of combining two observation images to generate a 3D image to stereoscopically view the subject.

In the endoscope, calibration (correction) for making an adjustment needs to be performed so that an image pickup apparatus displays expected images of an electronic acquired video on a monitor. Particularly, the 3D endoscope includes two left and right observation optical systems, and a deviation of image pickup optical axes of the observation optical systems needs to be calibrated.

When the 3D endoscope is for medical use in which the endoscope is inserted into a living body to conduct inspection, treatment, and the like, a sterilization and disinfection process, such as hydrogen peroxide sterilization and autoclave sterilization, is applied before the use as in a conventional endoscope. A load, such as thermal expansion, cooling, and pressure, caused by the sterilization and disinfection process may lead to a deviation in the image pickup optical axes of the two left and right observation optical systems.

To calibrate the image pickup optical axes of the endoscope, a processing apparatus is known as disclosed for example in Japanese Patent Application Laid-Open Publication No. 2008-104877, the processing apparatus configured to calibrate images recorded by an image pickup device and configured to use a calibration matrix (calibration markers) in a checkered pattern to correct intrinsic parameters and external parameters.

SUMMARY OF THE INVENTION

An aspect of the present invention provides an image calibration inspection tool including: a plurality of substantially rectangular markers including a plurality of projections and recesses, wherein two orthogonal sides of the plurality of markers are connected by an arc-shaped curve; and a calibration chart provided with the plurality of markers on a predetermined surface and in which two of the markers in a diagonal direction are disposed and separated by a predetermined distance.

An aspect of the present invention provides an endoscope system including: an image calibration inspection tool including: a plurality of substantially rectangular markers including a plurality of projections and recesses, wherein two orthogonal sides of the plurality of markers are connected by an arc-shaped curve; and a calibration chart provided with the plurality of markers on a predetermined surface and in which two of the markers in a diagonal direction are disposed and separated by a predetermined distance; an endoscope in which a distal end portion of an insertion portion can be attached to and detached from the image calibration inspection tool; and a control unit configured to correct an observation image acquired by the endoscope based on the calibration chart of the image calibration inspection tool photographed by the endoscope.

DETAILED DESCRIPTION OF THE PREFERRED EMBODIMENT(S)

Figure 1:
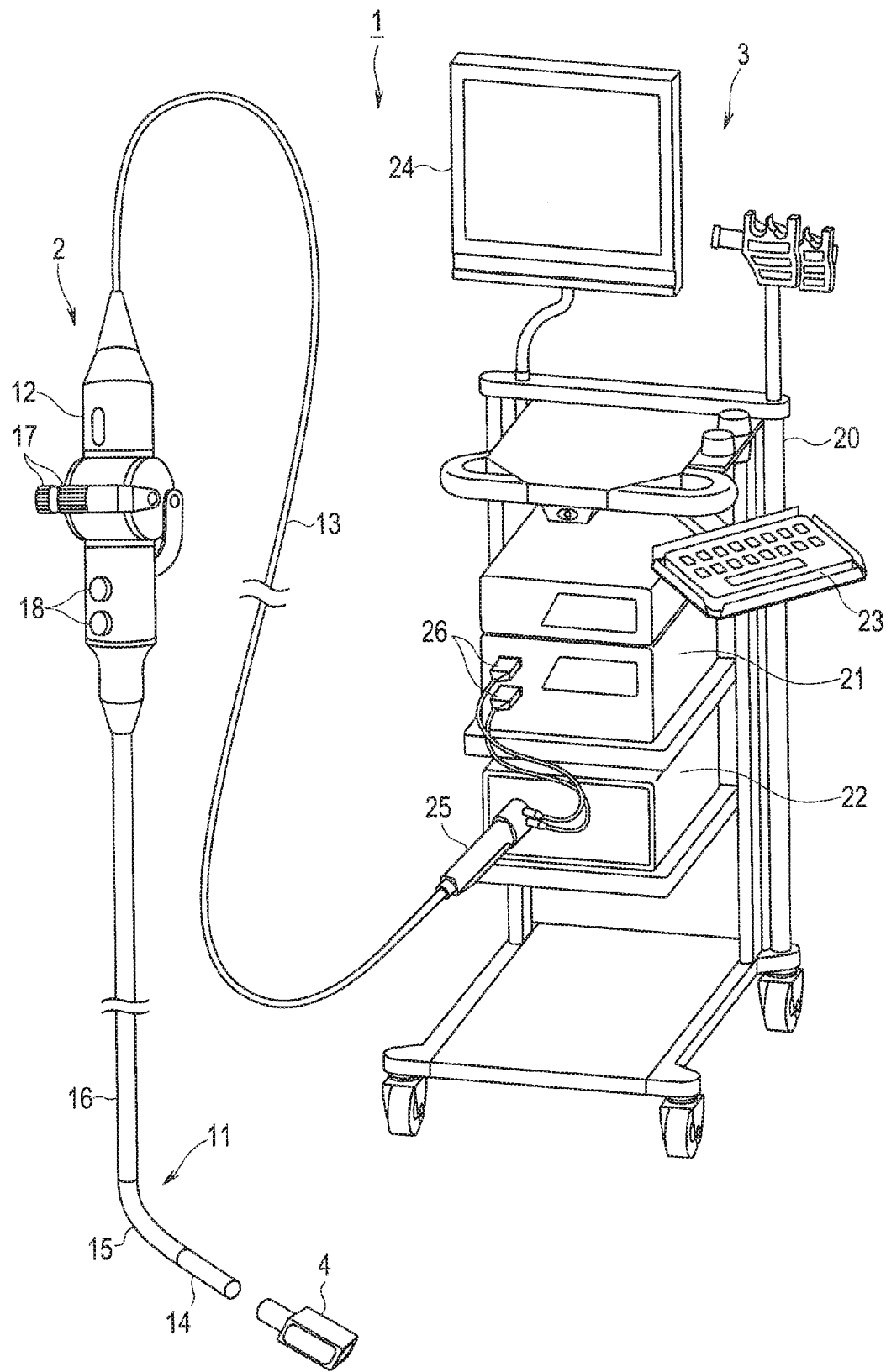
FIG. 1 is a perspective view showing a configuration of an endoscope system according to an aspect of the present invention.

Hereinafter, the present invention will be described with reference to the drawings. Note that scaling of each constituent element varies in each drawing used in the following description in order to illustrate each constituent element in a size that allows recognizing the constituent element on the drawing, and the present invention is not limited only to quantities of the constituent elements, shapes of the constituent elements, ratios of the sizes of the constituent elements, and relative positional relationships between respective constituent elements described in the drawings.

Figure 2:
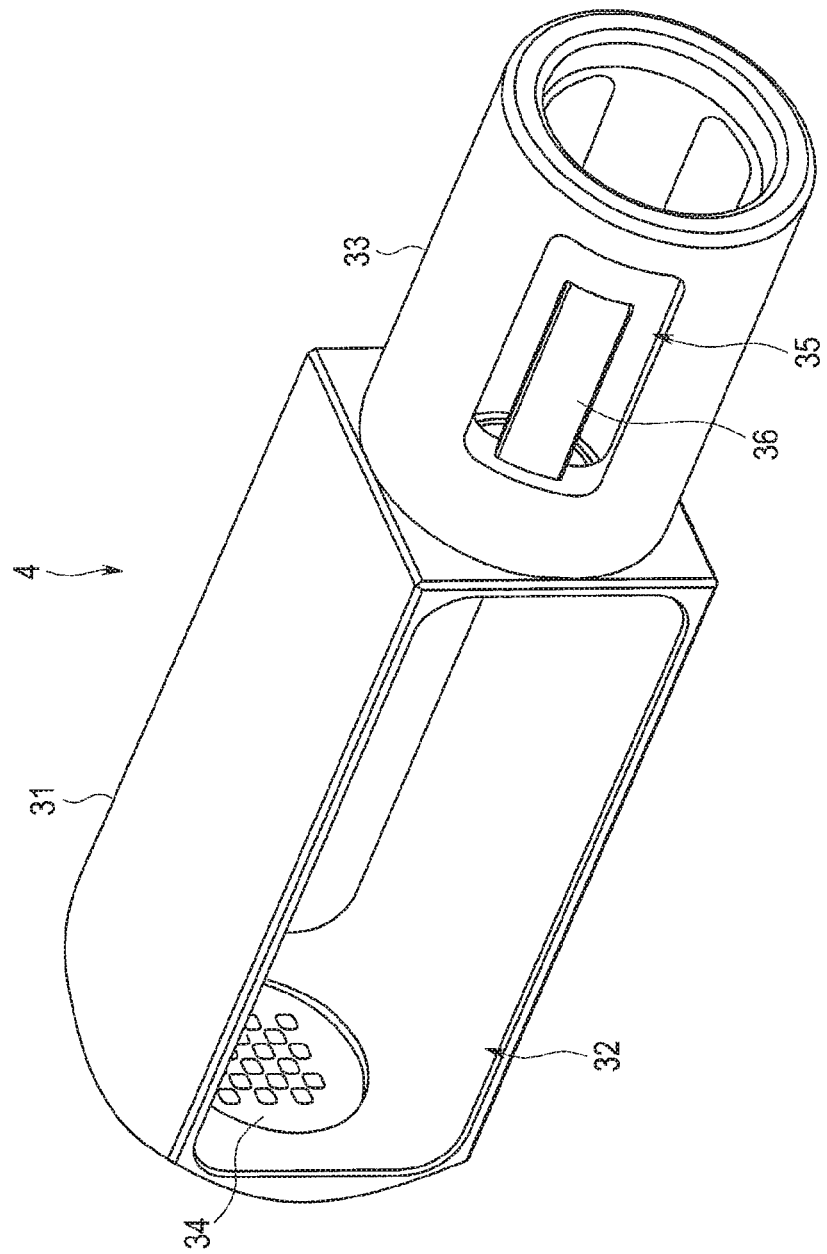
FIG. 2 is a perspective view showing a configuration of an image calibration inspection tool according to the aspect of the present invention.
Figure 3:
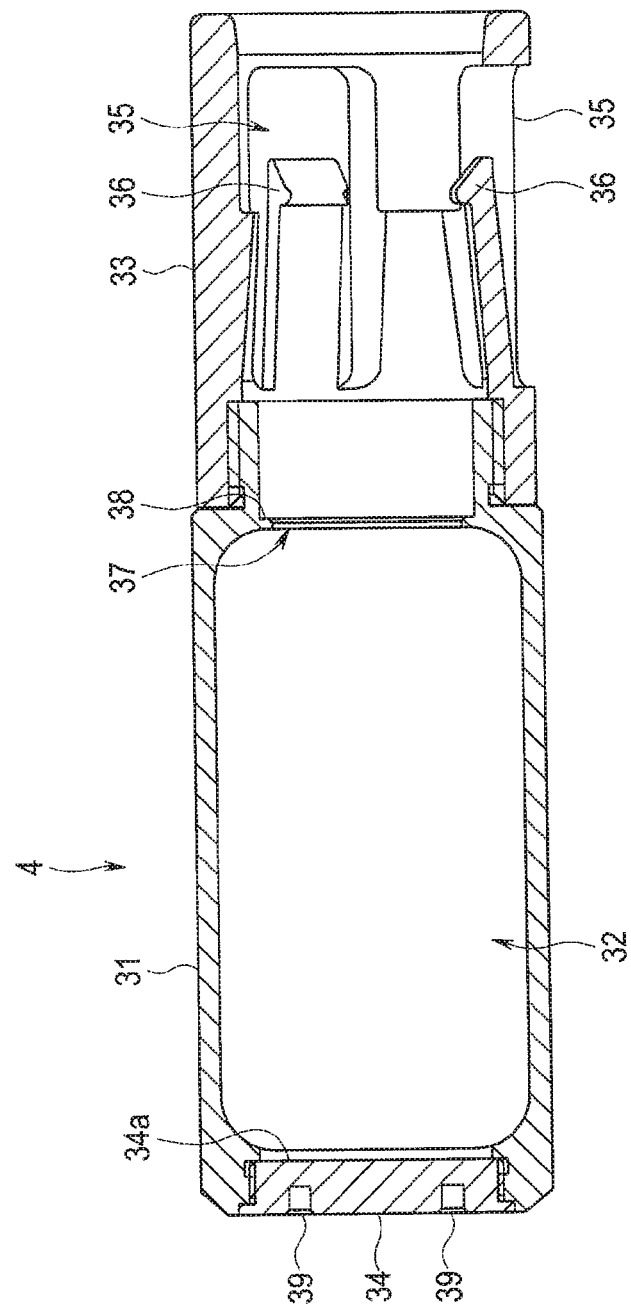
FIG. 3 is a cross-sectional view showing the configuration of the image calibration inspection tool according to the aspect of the present invention.
Figure 4:
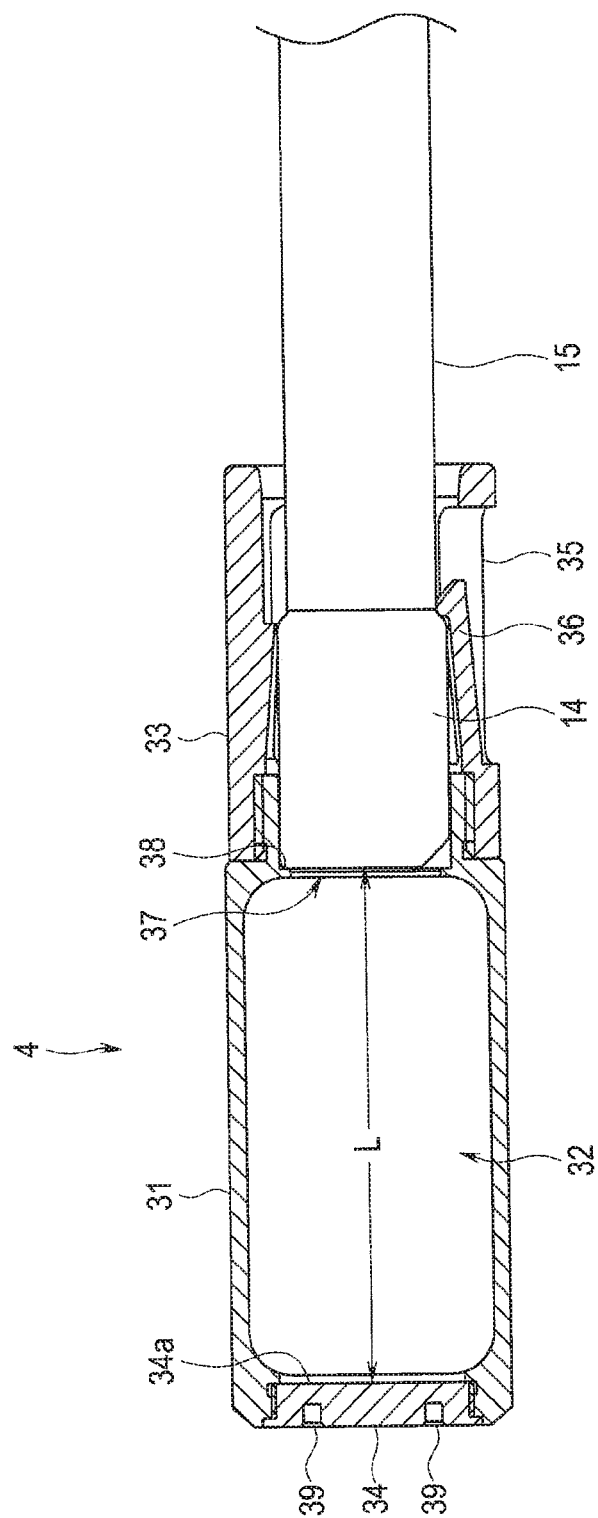
FIG. 4 is a cross-sectional view showing the configuration of the image calibration inspection tool installed on an insertion portion of an endoscope according to the aspect of the present invention.
Figure 5:
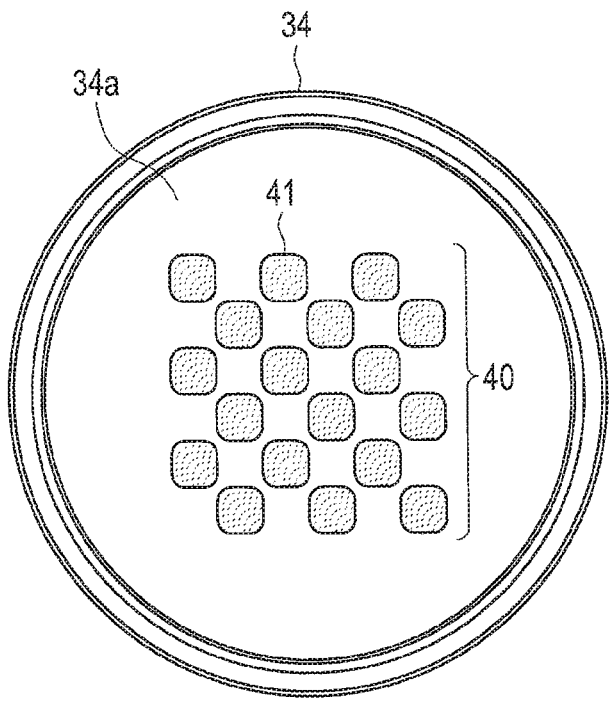
FIG. 5 is a plan view showing a calibration chart provided on a calibration chart surface of a calibration chart plate according to the aspect of the present invention.
Figure 6:
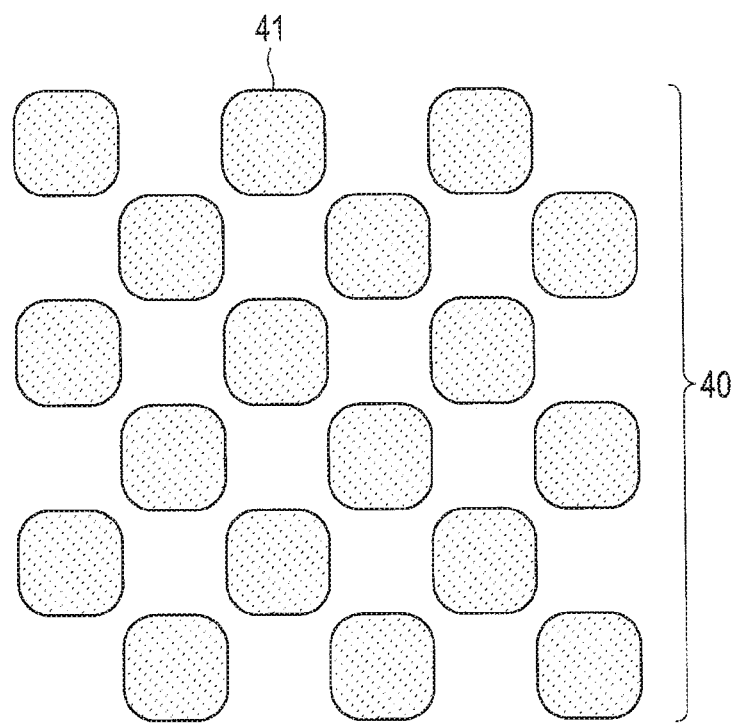
FIG. 6 is an enlarged plan view of the calibration chart according to the aspect of the present invention.
Figure 7:
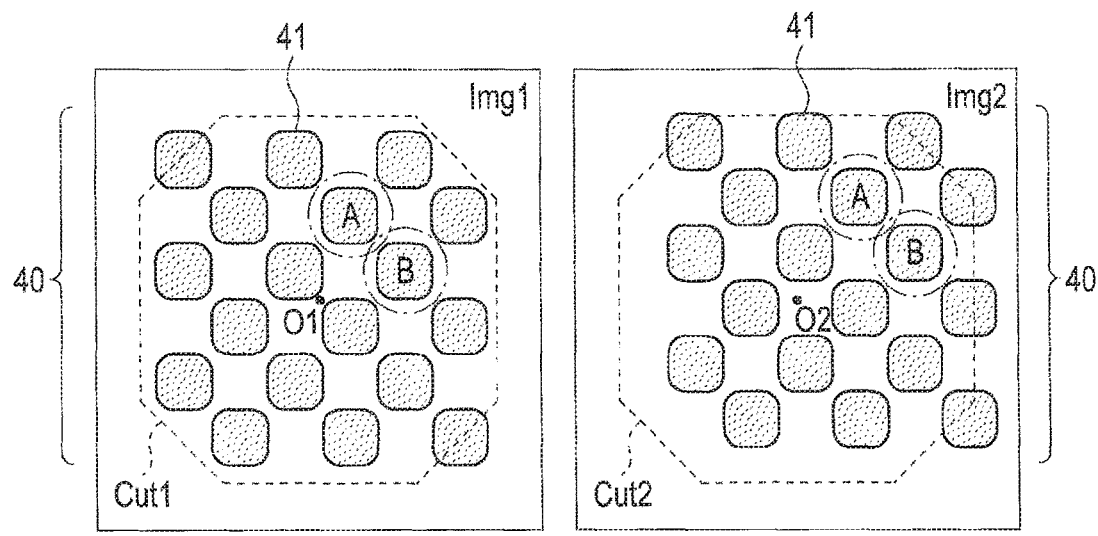
FIG. 7 is a diagram showing two image regions detected by image sensors in two observation optical systems according to the aspect of the present invention.
Figure 8:
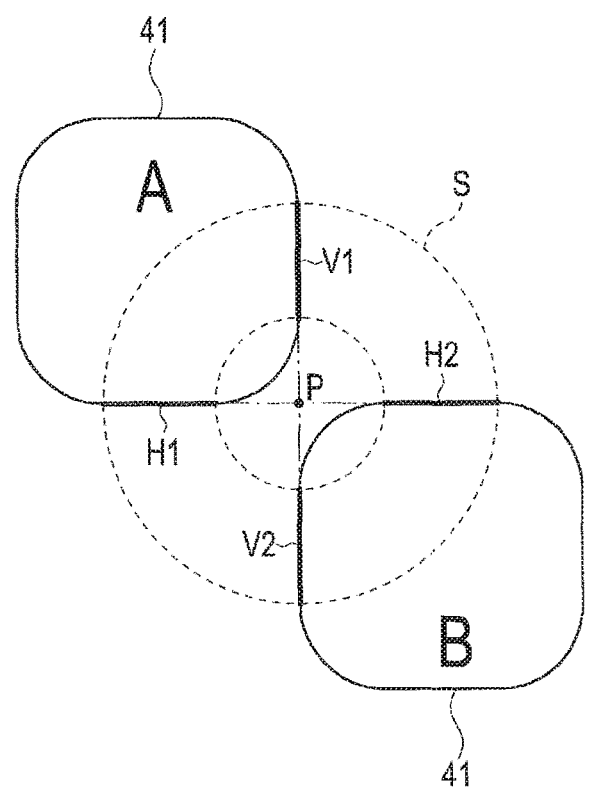
FIG. 8 is a diagram for describing a state of detecting an intersection point from two markers according to the aspect of the present invention.
Figure 9:
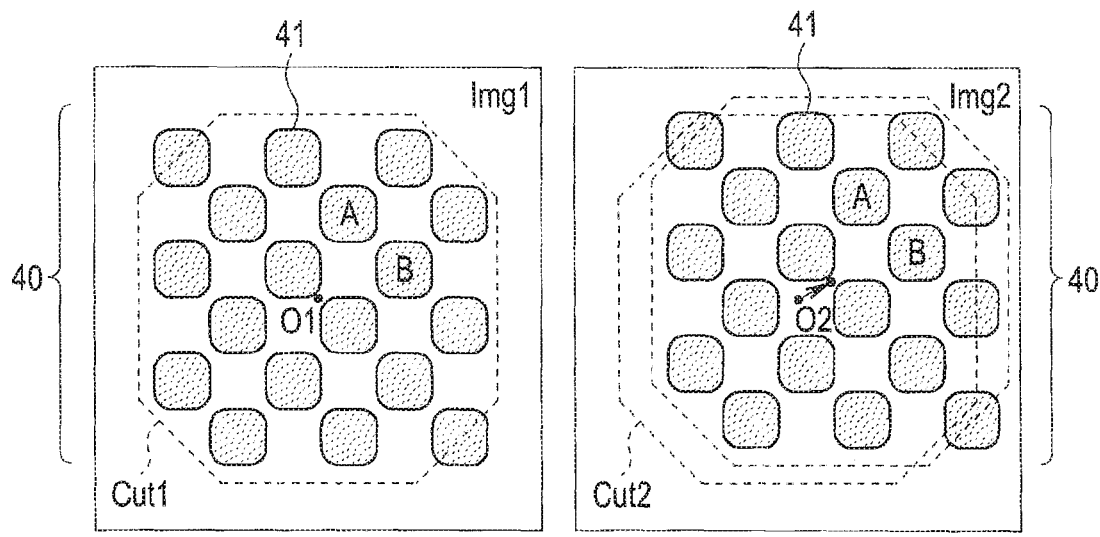
FIG. 9 is a diagram for describing a state of correcting acquired image regions according to the aspect of the present invention.
Figure 10:
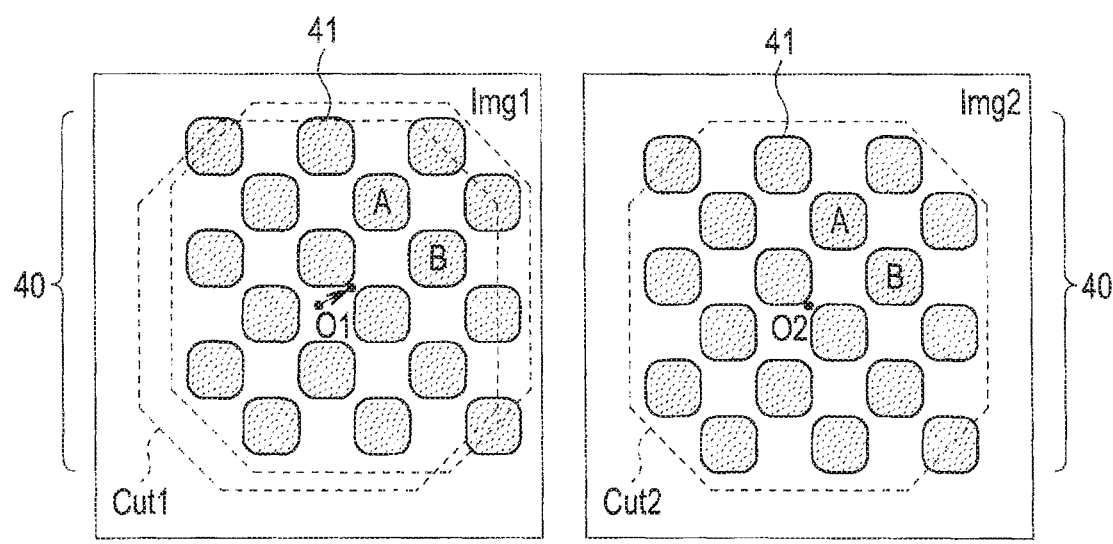
FIG. 10 is a diagram for describing another example of correcting the acquired image regions different from FIG. 9 according to the aspect of the present invention.
Figure 11:
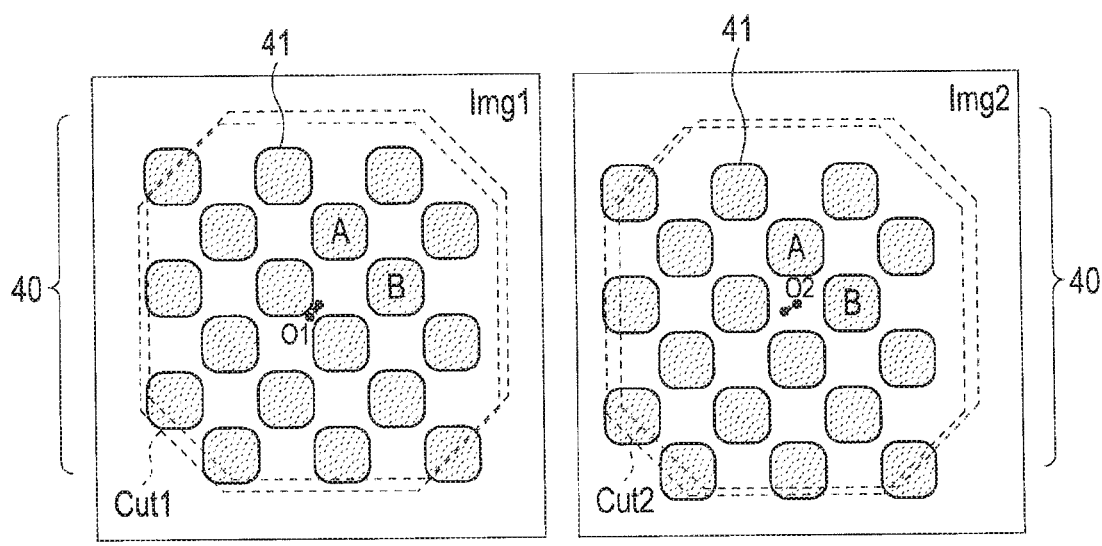
FIG. 11 is a diagram for describing another example of correcting the acquired image regions different from FIGS. 9 and 10 according to the aspect of the present invention.
Figure 12:
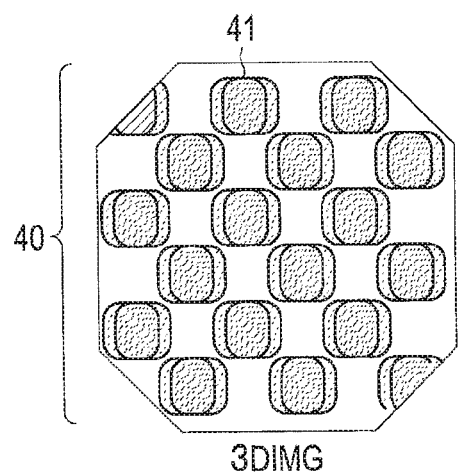
FIG. 12 is a diagram of a state in which two acquired image regions are combined according to the aspect of the present invention.
Figure 13:
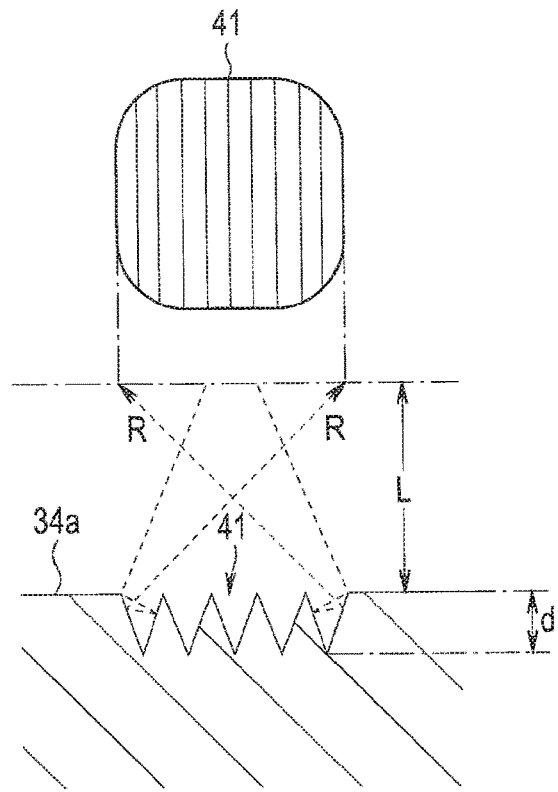
FIG. 13 is a diagram showing a first example of markers formed on the calibration chart surface of the calibration chart plate according to the aspect of the present invention.
Figure 14:
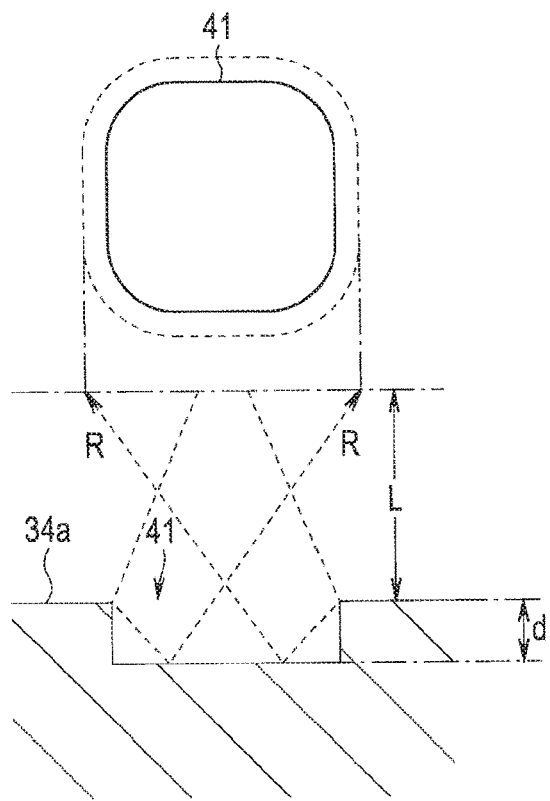
FIG. 14 is a diagram showing a second example of the markers formed on the calibration chart surface of the calibration chart plate according to the aspect of the present invention.
Figure 15:
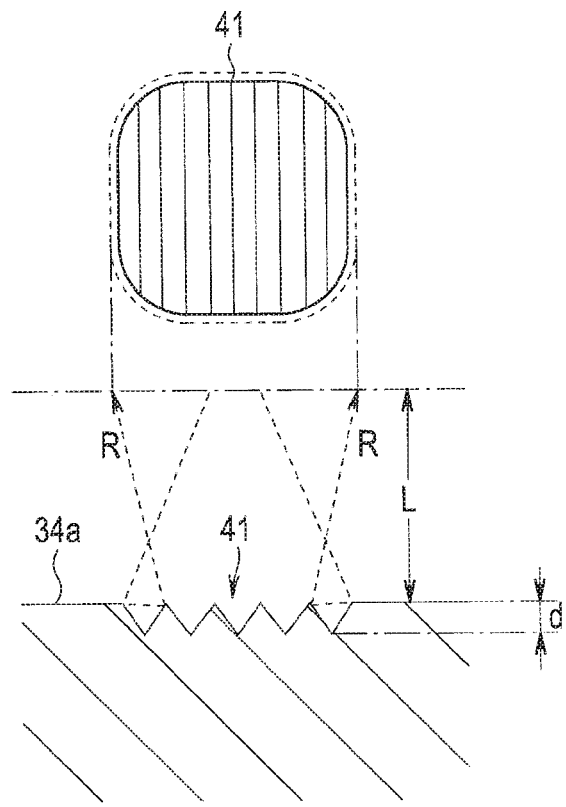
FIG. 15 is a diagram showing a third example of the markers formed on the calibration chart surface of the calibration chart plate according to the aspect of the present invention.
Figure 16:
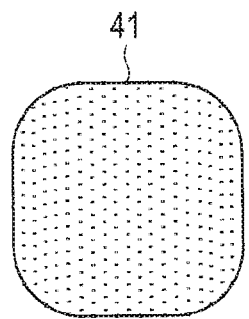
FIG. 16 is a diagram showing a fourth example of the markers formed on the calibration chart surface of the calibration chart plate according to the aspect of the present invention.

The drawings are related to an aspect of the present invention, wherein FIG. 1 is a perspective view showing a configuration of an endoscope system; FIG. 2 is a perspective view showing a configuration of an image calibration inspection tool; FIG. 3 is a cross-sectional view showing the configuration of the image calibration inspection tool; FIG. 4 is a cross-sectional view showing the configuration of the image calibration inspection tool installed on an insertion portion of an endoscope; FIG. 5 is a plan view showing a calibration chart provided on a calibration chart surface of a calibration chart plate; FIG. 6 is an enlarged plan view of the calibration chart; FIG. 7 is a diagram showing two image regions detected by image sensors in two observation optical systems; FIG. 8 is a diagram for describing a state of detecting an intersection point from two markers; FIG. 9 is a diagram for describing a state of correcting acquired image regions; FIG. 10 is a diagram for describing another example of correcting the acquired image regions different from FIG. 9; FIG. 11 is a diagram for describing another example of correcting the acquired image regions different from FIGS. 9 and 10; FIG. 12 is a diagram of a state in which two acquired image regions are combined; FIG. 13 is a diagram showing a first example of markers formed on the calibration chart surface of the calibration chart plate; FIG. 14 is a diagram showing a second example of the markers formed on the calibration chart surface of the calibration chart plate; FIG. 15 is a diagram showing a third example of the markers formed on the calibration chart surface of the calibration chart plate; and FIG. 16 is a diagram showing a fourth example of the markers formed on the calibration chart surface of the calibration chart plate.

As shown in FIG. 1, an endoscope system 1 includes an endoscope 2, a video system center 3, and an image calibration inspection tool 4 that is a calibration inspection tool. Note that the endoscope 2 here is a binocular 3D endoscope capable of combining two observation images to generate a 3D image to stereoscopically view a subject.

The endoscope 2 includes an insertion portion 11, an operation portion 12 consecutively provided on a proximal end of the insertion portion, and a universal cord 13 extended from the operation portion 12.

A distal end portion 14, a bending portion 15, and a rigid tube portion 16 are consecutively connected in the insertion portion 11 in order from a distal end. Note that although a so-called rigid endoscope used for surgery, in which the insertion portion 11 includes the rigid tube portion 16, is illustrated as the endoscope 2 here, the endoscope 2 is not limited to this, and the endoscope 2 may be a so-called flexible endoscope in which the insertion portion 11 is flexible.

The distal end portion 14 is provided with two observation windows and illumination windows on a distal end surface, and an image sensor, such as a CCD and a CMOS, provided on an image pickup apparatus detects two observation beams entering from the two observation windows through a plurality of objective optical systems (these are not shown).

The operation portion 12 includes two bending operation levers 17 for operating the bending portion 15 of the insertion portion 11 in an up and down direction (UD direction) as a first direction in an observation image and in a left and right direction (RL direction) as a second direction different from the first direction and substantially orthogonal to the first direction here in the observation image, in response to operation by an operator who is a doctor.

The operation portion 12 is further provided with buttons 18, such as a release switch, for operating the observation image.

The video system center 3 mainly includes: a video processor 21 as a control apparatus configured to control functions of various endoscopes 2 mounted on a trolley 20; a light source apparatus 22 including a light source of illumination light applied from the illumination windows of the distal end portion 14 of the endoscope 2 toward the subject; a keyboard 23; and a monitor 24.

The video processor 21 as the control apparatus is configured to control lighting of the light source apparatus 22 and configured to apply image processing to an image of the subject photographed through the endoscope 2 and display the image on the monitor 24.

Note that an extending end of the universal cord 13 of the endoscope 2 is provided with a light source connector 25 removably connected to the light source apparatus 22.

Two electrical cables 26 are extended from the light source connector 25 here, and each extending end of the electrical cables 26 is provided with an electrical connector 27 removably connected to the video processor 21.

Note that internal constituent elements of the endoscope 2 that is the 3D endoscope are similar to a conventional endoscope, and details of the constituent elements will not be described. The endoscope 2 is not limited to the 3D endoscope, and the endoscope 2 may be a 2D endoscope.

Next, a configuration of the image calibration inspection tool 4 will be described in detail based on FIGS. 2 to 4.

As shown in FIGS. 2 and 3, the entire image calibration inspection tool 4 is formed by metal, such as stainless steel, that is hard to rust or a heat-resistant chemical-resistant resin to provide autoclave sterilization resistance, and the image calibration inspection tool 4 mainly includes: a rectangular inspection tool body portion 31 provided with opening portions 32 on both side portions; a cylindrical endoscope connection portion 33 screwed and fixed to a proximal end side of the inspection tool body portion 31; and a disc-shaped calibration chart plate 34 screwed and fixed to a distal end wall of the inspection tool body portion 31.

The existence of the opening portions 32 facilitates cleaning and can prevent unnecessary reflection of illumination light at both side portions of the inspection tool body portion 31.

Three opening portions 35 are formed here on the endoscope connection portion 33 at substantially even intervals in a circumferential direction, and a claw portion 36 inclined in an inner diameter direction is provided in each of the opening portions 35.

The claw portions 36 are elastically deformed in an outer diameter direction of the endoscope connection portion 33 when the distal end portion 14 of the endoscope 2 is inserted into the endoscope connection portion 33, and the claw portions 36 lock a proximal end circumferential direction of the distal end portion 14 to mechanically fix the distal end portion 14 based on a so-called snap-fit system (see FIG. 4).

Note that the distal end portion 14 is fixed by the endoscope connection portion 33 such that a distal end surface comes into contact with a wall portion 38 as a contact portion around a proximal end opening portion 37 of the inspection tool body portion 31. The existence of three claw portions 36 allows stable contact of the distal end portions 14.

As a result, a predetermined distance L from the distal end surface to the calibration chart plate 34 is always constant in the distal end portion 14 of the endoscope 2 installed on the image calibration inspection tool 4. That is, when the endoscope 2 is installed on the image calibration inspection tool 4, the predetermined distance L to the calibration chart surface 34a of the calibration chart plate 34 is always constant, and the endoscope 2 can photograph a calibration chart 40 described later provided on a calibration chart surface 34a to accurately calibrate an acquired image.

The calibration chart plate 34 arranged on a distal end surface of the inspection tool body portion 31 is provided with, on a distal end surface side that is a front surface, two recessed portions 39 into which jigs are inserted when the calibration chart plate 34 is screwed and fixed to the inspection tool body portion 31.

As shown in FIGS. 5 and 6, the calibration chart plate 34 is provided with the calibration chart 40 that is a calibration marker including a plurality of substantially rectangular markers 41 arranged in so-called lattice pattern and checkered pattern, wherein the markers 41 are formed by machining, laser marking, or the like on the calibration chart surface 34a on a proximal end surface that is a back surface.

A corner portion of each of the markers 41 is formed in an arc-shaped curve such that the markers 41 adjacent to each other in a diagonal direction are separated at a predetermined distance and such that two orthogonal sides are connected.

As a result, the markers 41 can be formed by various machining, laser marking, or the like without generation of distorted shapes due to crushing, edges, or the like at the corner portions of the markers 41 adjacent to each other in the diagonal direction.

That is, when the calibration chart 40 in the checkered pattern is formed by various machining, laser marking, or the like so as to strictly form the corner portions of the markers 41 adjacent to each other in the diagonal direction, the corner portions of two markers 41 overlap with each other, and distorted shapes are generated due to crushing, edges, or the like.

When the distorted shapes due to crushing, edges, or the like are generated in the calibration chart 40, the illumination light of the endoscope 2 is reflected, and a desired observation image cannot be accurately obtained. Or the corner portions are crushed, and detection accuracy of the corner portions is deteriorated.

Furthermore, when the arcs of the corner portions of the markers 41 are enlarged to increase the distance between the adjacent markers 41 in the diagonal direction, each of linear sides of the markers 41 is shortened, and the detection accuracy of the calibration chart 40 is deteriorated.

Note that when the corner portions of the markers 41 adjacent to each other in the diagonal direction are formed to overlap with each other, the sides of two markers 41 are not linear, and a difference equivalent to the overlapped width is generated. Therefore, orthogonality is lost, and an accurate function of the calibration chart 40 is lost.

Therefore, the plurality of markers 41 forming the calibration chart 40 are formed on the calibration chart surface 34a of the calibration chart plate 34 by various machining, laser marking, or the like such that each of the linear sides is arranged on a straight line and has orthogonality and such that the corner portions have a shape set to an arch shape with an optimal radius of curvature to provide a sufficient length that allows detection according to an observation performance of the endoscope 2.

Furthermore, the arrangement of the plurality of markers 41 allows detection by other markers 41 even if part of the markers 41 cannot be detected due to a defect, deterioration, or the like. In this case, the size of the markers 41 needs to be set to a size larger than a supposed amount of deviation to prevent mistaking the markers 41 for other markers.

Therefore, the calibration chart 40 provided with the plurality of markers 41 does not have a distorted part that unnecessarily reflects the illumination light of the endoscope 2, and the calibration chart 40 is formed on the calibration chart surface 34a of the calibration chart plate 34 to allow accurately detecting each side of each marker 41.

A calibration method of an observation image of the endoscope 2 of the endoscope system 1 configured as described above will be described in detail. Note that since the endoscope 2 is a 3D endoscope here, a method of calibrating a deviation of image pickup optical axes of observation optical systems will be described.

First, the image calibration inspection tool 4 is installed on the distal end portion 14 of the insertion portion 11 of the endoscope 2. The endoscope 2 then photographs the calibration chart 40 of the image calibration inspection tool 4.

As shown in FIG. 7, for example, a first acquired image region Img1 of a first observation optical system and a second acquired image region Img2 of a second observation optical system detected by the image sensor of the image pickup apparatus of the endoscope 2 are inputted to the video processor 21.

In this case, a control unit in the video processor 21 sets centers O1 and O2 of a first image region Cut1 cut out from the first acquired image region Img1 and a second image region Cut2 cut out from the second acquired image region Img2, respectively, such that the centers O1 and O2 coincide with each other.

From this state, the control unit in the video processor 21 selects two markers 41 (A, B) of the calibration chart 40 from the first image region Cut1 and the second image region Cut2.

Note that when there is a distortion due to optical characteristics of the observation optical systems, it is preferable in terms of calibration accuracy that the markers 41 to be selected be selected from markers close to the centers O1 and O2 of the respective image regions.

The control unit then detects two linear sides V1 and H1 of a first marker 41 (A) and two linear sides V2 and H2 of a second marker 41 (B) as shown in FIG. 8.

Note that an algorithm of a donut-shaped search range S is set here as a program for detecting positions in order to detect the linear sides V1, V2, H1, and H2 of the two markers 41 (A, B), respectively.

The control unit uses the donut-shaped search range S to detect a position of an intersection point P where an extension of the side V1 in the vertical direction of the first marker 41 (A) and the side V2 in the vertical direction of the second marker 41 (B) and an extension of the side H1 in the horizontal direction of the first marker 41(A) and the side H2 in the horizontal direction of the second marker 41 (B) are orthogonal to each other.

According to the detection method, the intersection point P of the markers 41 can be detected based on the donut-shaped search range S even when a position in a rotation direction of the image calibration inspection tool 4 with respect to the endoscope 2 is not determined.

Next, the control unit detects a deviation of the position of the intersection point P and the position of the center O2 of the second image region Cut2 with respect to the position of the intersection point P and the position of the center O1 of the first image region Cut1 and makes a correction to bring one of the image regions into line with the other image region.

For example, as shown in FIG. 9, the control unit corrects the positions to bring the center O1 of the first image region Cut1 and the center O2 of the second image region Cut2 into line with each other and changes the position cut out from the second acquired image region Img2.

Note that the example of control is just an example, and for example, the first image region Cut1 may be brought into line with the second image region Cut2 to change the position cut out from the first acquired image region Img1 as shown in FIG. 10. For example, both of the positions of the first image region Cut1 and the second image region Cut2 may be changed as shown in FIG. 11.

Note that the amount of cutout is smaller when both of the positions are changed, and the cutout range can be effectively utilized.

Furthermore, although the example of control by the video processor 21 is described, the control is not limited to this, and for example, a control unit may be provided on the operation portion 12 of the endoscope to perform the control.

In this way, for example, the video processor 21 generates a 3D video by combining the first image region Cut1 and the second image region Cut2 as shown in FIG. 12 and causes the monitor 24 to display the 3D video.

Note that although the example of controlling the image calibration of the endoscope 2 that is a 3D endoscope is described above, it is obvious that the image calibration inspection tool 4 can also perform the image calibration of a 2D endoscope.

Here, an example of forming the plurality of markers 41 forming the calibration chart 40 on the calibration chart surface 34a of the calibration chart plate 34 through various machining, laser marking, or the like will be described.

As shown in FIG. 13, it is preferable to shave off the calibration chart surface 34a of the calibration chart plate 34 to form a plurality of linear shapes to form projections and recesses triangular in cross section for the plurality of markers 41 through various machining, laser marking, or the like to generate contrast in the calibration chart 40 through reflection of light and burning (coloring).

That is, a line drawing process is applied to the plurality of markers 41 by shaving off the calibration chart surface 34a of the calibration chart plate 34, and reflection components of the illumination light are attenuated. Therefore, a diffraction image caused by the reflection of the illumination light is improved, and a contour can be accurately displayed.

More specifically, reflected light R of the illumination light applied to the plurality of markers 41 enters the objective optical system from the observation windows of the endoscope 2 and forms a reflected image.

In this case, a depth d of the linearly formed projections and recesses triangular in cross section forming the markers 41 can be an optimal depth with respect to the distance L to the observation windows of the distal end portion 14 of the endoscope 2 to allow clearly photographing the contrast of the calibration chart 40 based on the plurality of markers 41 to perform accurate image correction.

Furthermore, the plurality of markers 41 may be formed by a line drawing process through etching, wire electric discharge machining, and the like other than various machining, laser marking, or the like. Note that if the plurality of markers 41 are formed by chromium deposition, black alumite, or the like, the plurality of markers 41 are discolored due to hydrogen peroxide sterilization and autoclave sterilization, and the desired contrast of the calibration chart 40 cannot be obtained.

Furthermore, if the plurality of markers 41 are simply formed in a recessed portion shape as shown for example in FIG. 14, the plurality of markers 41 are easily affected by the diffraction caused by the illumination light. The reflected light R exceeds the range of the markers 41 and enters the objective optical system from the observation windows of the endoscope 2, and the reflected image formed is an expanded image.

In addition, if the depth d of the linearly formed projections and recesses triangular in cross section forming the plurality of markers 41 is too shallow as shown for example in FIG. 15, the reflected light R exceeds the range of the markers 41 and enters the objective optical system from the observation windows of the endoscope 2, and the reflected image formed is an expanded image.

In this way, if the plurality of markers 41 are detected in the expanded state, the coordinates of the intersection point P of the calibration chart 40 are deviated, and the image cannot be accurately corrected.

Therefore, the image calibration inspection tool 4 of the present embodiment is configured to solve the problems, wherein the projections and recesses are formed on the calibration chart 40 by drawing lines with the depth d optimal with respect to the separation distance L to the endoscope 2 through machining, laser marking, or the like to allow clearly photographing the contrast of the calibration chart 40.

Note that the markers 41 may be formed not only in the linear shape. For example, a plurality of conical recessed portions with the depth d may be formed on the calibration chart surface 34a of the calibration chart plate 34 through continuous dot-like processing as shown in FIG. 16.

Furthermore, surface treatment, such as sandblasting, glass beading, chemical polishing, and barreling, can be applied to parts of the calibration chart surface 34a of the calibration chart plate 34 other than the plurality of markers 41 forming the calibration chart 40 to scatter the illumination light to reduce the reflection.

As described, the endoscope system 1 of the present embodiment includes the image calibration inspection tool 4 in which the calibration chart 40 is formed by machining, laser marking, or the like to handle the sterilization and disinfection process, such as hydrogen peroxide sterilization and autoclave sterilization, and accurate image calibration of the endoscope 2 can be performed. Therefore, the endoscope system 1 including the image calibration inspection tool 4 as a calibration inspection tool has sterilization and disinfection resistance and can accurately calibrate the image.

The invention described in the embodiment is not limited to the embodiment and modifications, and the invention can be modified in various ways in an execution phase without departing from the scope of the invention. Furthermore, the embodiment includes inventions of various phases, and various inventions can be extracted based on appropriate combinations of a plurality of disclosed constituent conditions.

For example, when the described problems can be solved, and the described advantageous effects can be obtained even if some of the constituent conditions illustrated in the embodiment are deleted, the configuration after the deletion of the constituent conditions can be extracted as an invention.

What is claimed is:

1. An image calibration inspection tool comprising:
    a plurality of substantially rectangular markers including a plurality of projections and recesses having a depth with respect to a predetermined surface, wherein two orthogonal sides of the plurality of markers are connected by an arc-shaped curve; and
    a calibration chart provided with the plurality of markers on the predetermined surface and in which two of the markers in a diagonal direction are formed and separated by a predetermined distance.

2. The image calibration inspection tool according to claim 1,
    wherein the markers forming the calibration chart are arranged in a checkered pattern.

3. The image calibration inspection tool according to claim 1,
    wherein a line drawing process is applied to the markers based on the plurality of projection and recesses triangular in cross section.

4. The image calibration inspection tool according to claim 3,
    wherein continuous dot-like processing is applied to the markers based on a conical recessed portion.

5. An endoscope system comprising:
    the image calibration inspection tool according to claim 1;
    an endoscope in which a distal end portion of an insertion portion can be attached to and detached from the image calibration inspection tool; and
    a control unit configured to correct an observation image acquired by the endoscope based on the calibration chart of the image calibration inspection tool photographed by the endoscope.

6. The endoscope system according to claim 5,
    wherein the endoscope is a 3D endoscope comprising two observation optical systems.

7. The image calibration inspection tool according to claim 1,
    wherein the projections and recesses of the plurality of markers are formed by shaving off the calibration chart by a line drawing process.

8. The image calibration inspection tool according to claim 1,
    wherein each of sides of the plurality of markers are arranged linearly such that the markers have orthogonality.

9. The image calibration inspection tool according to claim 1,
    wherein the depth of the projections and recesses of the markers is set according to a predetermined distance between the predetermined surface and a position at which an image of the calibration chart is picked up.

10. The image calibration inspection tool according to claim 9, further comprising:
    a body portion provided with the predetermined surface;
    an endoscope connection portion connected to the body portion and to which a distal end portion of an insertion portion of an endoscope is removably installed and fixed; and
    a contact portion coming into contact with a distal end surface of the distal end portion in a state in which the distal end portion is fixed to the endoscope connection portion,
    wherein the predetermined distance is defined by the calibration chart formed on the predetermined surface and by an observation window provided on the distal end portion in contact with the contact portion.

* * * * *